US00PP31440P2

(12) United States Plant Patent
Danziger

(10) Patent No.: US PP31,440 P2
(45) Date of Patent: Feb. 11, 2020

(54) ***CALIBRACHOA* PLANT NAMED 'DCALBUBGM'**

(50) Latin Name: ***Calibrachoa* hybrid**
Varietal Denomination: DCALBUBGM

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 16/350,160

(22) Filed: Oct. 4, 2018

(51) Int. Cl.
*A01H 5/02* (2018.01)
*A01H 6/82* (2018.01)

(52) U.S. Cl.
USPC ..... Plt./413

(58) Field of Classification Search
USPC ..... Plt./413
CPC . A01H 5/02; A01H 5/025; A01H 5/12; A01H 6/82
See application file for complete search history.

(56) References Cited

U.S. PATENT DOCUMENTS

PP21,502 P2 * 11/2010 Dummen ..... A01H 5/02 Plt./413

OTHER PUBLICATIONS

Danziger Annuals & Bedding Plants North America Lia Series, retrieved on Jul. 16, 2019, retrieved from the Internet at https://danzigeronline.com/catalog/annuals-usa/all/?crop_id=lia-series, 2 pp. (Year: 2019).*

Knox Horticulture Young Plant Programs 2018-2019, retrieved on Jul. 16, 2019, retrieved from the Internet at https://www.knoxhort.com/wp-content/uploads/Documents/KnoxHort_YP-Program-Brochure.pdf, cover page, pp. 24, 53-60. (Year: 2019).*

RHS *Calibrachoa* Aloha Classic Tiki Hot Pink, retrieved on Jul. 16, 2019, retrieved from the Internet at https://www.rhs.org.uk/Plants/281327/i-Calibrachoa-i-Font-Face-times-New-Roman-Aloha-Classic-Tiki-Hot-Pink-FONT-Duealtihotpi-sup-(PBR)-sup-(Aloha-Classic-Series)/Details, 2 pp. (Year: 2019).*

Screen captures from YouTube video clip entitled "Lia *Calibrachoa*" uploaded on Jul. 16, 2019, retrieved from the Internet at https://www.youtube.com/watch?v=C0V8czcQgJA, one page. (Year: 2018).*

* cited by examiner

*Primary Examiner* — June Hwu
(74) *Attorney, Agent, or Firm* — Cassandra Bright

(57) ABSTRACT

A new and distinct *Calibrachoa* cultivar named 'DCALBUBGM' is disclosed, characterized by a semi-trailing plant habit. Plants produce an abundance of large pink colored flowers with a yellow center and throat. Plants begin flowering early, have strong branches and are day length neutral. The new variety is a *Calibrachoa*, normally produced as an outdoor garden or container plant.

2 Drawing Sheets

Figure 1:
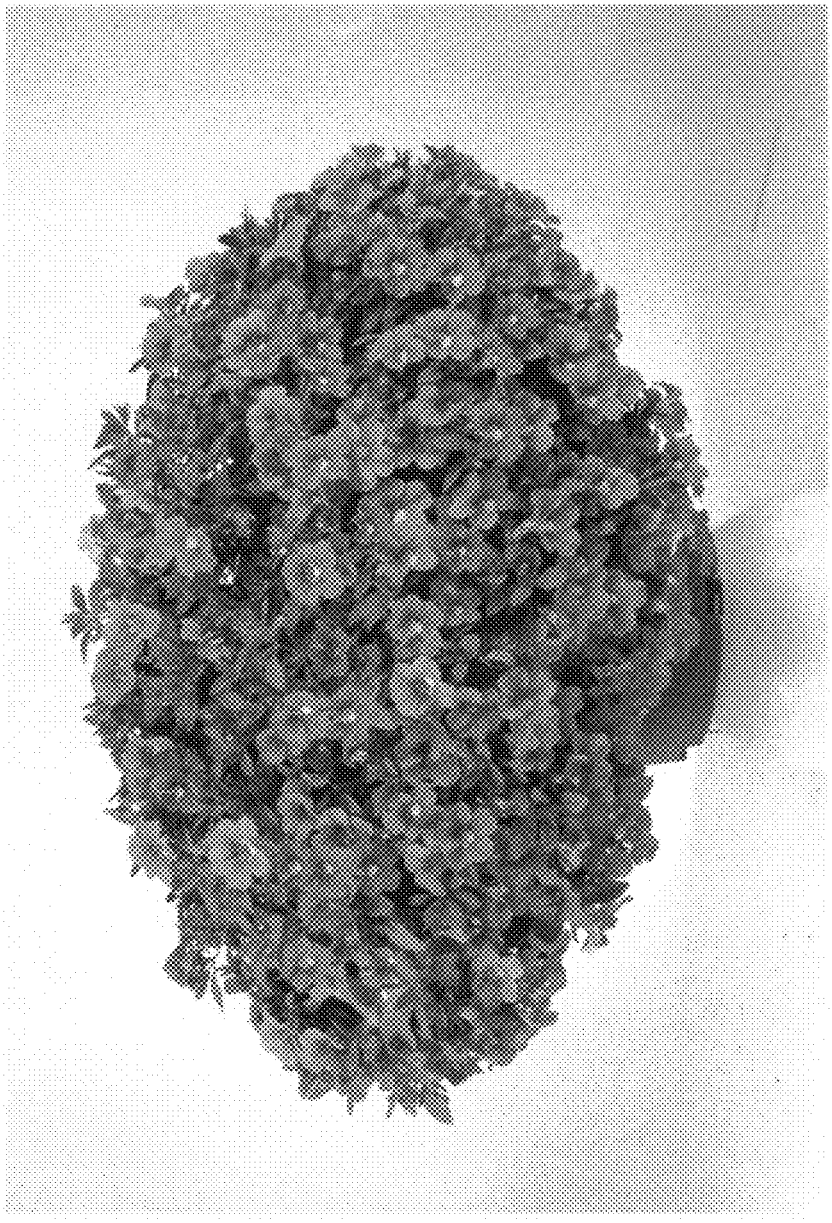

Latin name of the genus and species: *Calibrachoa* hybrid.
Variety denomination: 'DCALBUBGM'.

BACKGROUND OF THE INVENTION

The new *Calibrachoa* cultivar is a product of a planned breeding program conducted by the inventor, Gavriel Danziger in Moshav Mishmar Hashiva, Israel. The objective of the breeding program was to produce new *Calibrachoa* varieties. The cross resulting in this new variety was made during January of 2014.

The seed parent is the unpatented, propriety variety referred to as *Calibrachoa* 'cv. 14-4051'. The pollen parent is the unpatented, propriety variety referred to as *Calibrachoa* 'cv. 14-4050'. The new variety was discovered in March of 2015 by the inventor in a group of seedlings resulting from the parental crossing, in a greenhouse in Moshav Mishmar Hashiva, Israel.

Asexual reproduction of the new cultivar 'DCALBUBGM' was first performed by terminal vegetative cuttings during March of 2015, at a greenhouse in Moshav Mishmar Hashiva, Israel. Subsequent propagation by has shown that the unique features of this cultivar are stable and reproduced true to type in successive generations. First public access to plants of the variety occurred Nov. 12, 2017 in the United States. This offer came directly or indirectly from the inventor, qualifying for the exception allowed under 102(b). Previous to this sale, although the variety may have been publicized in print, plants were not available to the public for propagation.

SUMMARY OF THE INVENTION

The cultivar 'DCALBUBGM' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCALBUBGM' These characteristics in combination distinguish 'DCALBUBGM' as a new and distinct *Calibrachoa* cultivar:

1. Large pink flowers with a yellow throat.
2. Early flowering.
3. Flowering can begin under 10-hour day length, day-length neutral for this market class.
4. Semi-trailing plant habit.
5. Medium vigor.

PARENT COMPARISON

Plants of the new cultivar 'DCALBUBGM' are similar to plants of the seed parent in most horticultural characteristics, however, plants of the new cultivar 'DCALBUBGM' differ in the following;

1. The new variety has a semi-trailing growth habit; the seed parent is compact, mounding.
2. New variety has pink flowers; seed parent has white flowers.
3. The new variety has larger flowers than the seed parent.
4. The seed parent has a lower vigor than the new variety.

Plants of the new cultivar 'DCALBUBGM' are similar to plants of the pollen parent in most horticultural characteristics however, plants of the new cultivar 'DCALBUBGM' differ in the following;

1. The new variety has a semi-trailing growth habit; the pollen parent is compact.
2. The new variety has pink flowers; the pollen parent has white flowers with pink eyes.
3. The new variety has larger flowers than the pollen parent.
4. The pollen parent has a lower vigor than the new variety.

COMMERCIAL COMPARISON

Plants of the new cultivar 'DCALBUBGM' can be compared to the patented commercial variety *Calibrachoa* 'DANOA49' U.S. Plant Pat. No. 22,050. These varieties are similar in most horticultural characteristics; however, 'DCALBUBGM' differs in the following:

1. 'DCALBUBGM' is earlier to flower in comparison to 'DANOA49'.
2. 'DCALBUBGM' is day length neutral, while 'DANOA49' is not.
3. 'DCALBUBGM' has a bigger flower than 'DANOA49'.
4. 'DCALBUBGM' has a semi-trailing habit, while 'DANOA49' is trailing.

Plants of the new cultivar 'DCALBUBGM' can also be compared to the commercial variety *Calibrachoa* 'Duealtihotpi', U.S. Plant Pat. No. 21,502. These varieties are similar in most horticultural characteristics; however, 'DCALBUBGM' differs in the following:

1. 'DCALBUBGM' is day length neutral; 'Duealtihotpi' is not.
2. 'DCALBUBGM' has a more vivid pink color than 'Duealtihotpi'.
3. 'DCALBUBGM' has a semi-trailing habit, while 'Duealtihotpi' is trailing.
4. 'DCALBUBGM' is more vigorous than 'Duealtihotpi'.

BRIEF DESCRIPTION OF THE PHOTOGRAPHS

The accompanying photograph in FIG. 1 illustrates in full color a typical plant in a 20 cm pot, at approximately 5 months of age, of 'DCALBUBGM' grown in a greenhouse, in Moshav Mishmar Hashiva, Israel.

Figure 2:
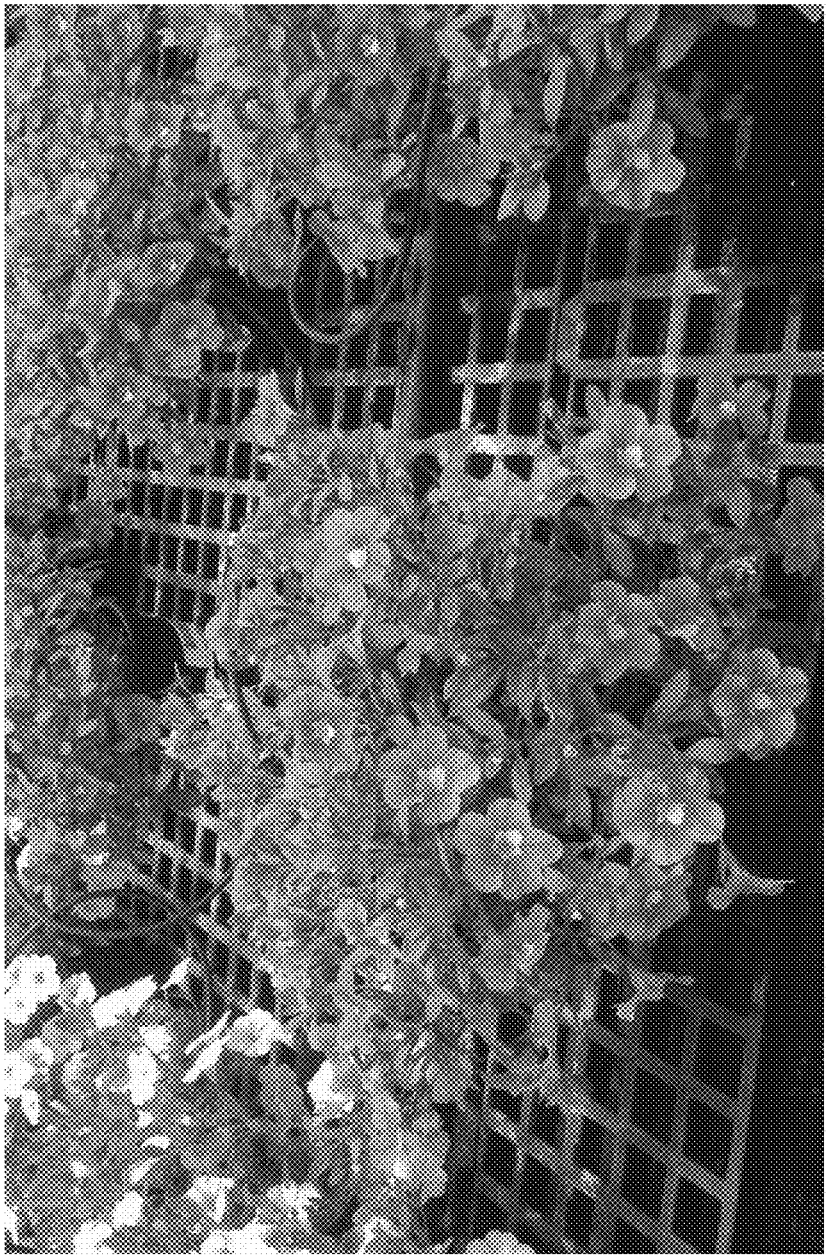

FIG. 2 illustrates in full color typical flowering plants of 'DCALBUBGM' grown in 12 cm pots in early Spring, during days having 10 hours of light.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DCALBUBGM' plants grown in greenhouse in Moshav Mishmar Hashiva, Israel, under natural lighting. Measurements were taken during Summer of 2018. The plants were approximately 60 days from a rooted cutting in a 15 cm pot. The growing temperature ranged from 15° C. to 28° C. during the days, 15° C. to 20° C. during the nights. Measurements and numerical values represent averages of typical plant types.

Botanical classification: *Calibrachoa* hybrid 'DCALBUBGM'.

PROPAGATION

Time to initiate roots: 10 to 15 days at approximately 18° C.
Root description: Fibrous.

PLANT

Growth habit: Semi-trailing.
Pot size of plant described: 12 cm.
Height: About 12 cm to top of flowering plane.
Plant spread: 44 cm.
Growth rate: Fast, moderately vigorous.
Length of primary lateral branches: 18 cm.
Diameter of lateral branches: 0.2 to 0.3 cm.
Quantity of primary lateral branches: 10.
Characteristics of primary lateral branches:
*Form*.—Cylindrical-laterally compressed.
*Diameter*.—0.2 to 0.3 cm.
*Color*.—RHS Yellow-Green 146B.
*Texture*.—Hispid.
*Strength*.—Good, flexible.
Internode length: 2 to 2.5 cm.

FOLIAGE

Leaf:
*Arrangement*.—Alternate.
*Quantity*.—Approximately 60 per branch.
*Average length*.—3.5 cm.
*Average width*.—1.3 cm.
*Shape of blade*.—Elliptic.
*Apex*.—Rounded.
*Base*.—Acuminate.
*Margin*.—Entire.
*Texture of top surface*.—Glabrous.
*Texture of bottom surface*.—Scabrous.
*Aspect*.—90 degrees.
*Color*.—Young foliage upper side: RHS Yellow-Green 146A. Young foliage under side: RHS Yellow-Green 147C. Mature foliage upper side: RHS Yellow-Green 137B. Mature foliage under side: RHS Yellow-Green 137D.
*Venation*.—Type: Pinnate. Venation color upper side: RHS Yellow-Green 137B. Venation color under side: RHS Yellow-Green 137D.

*Petiole*.—Length: 0.5 to 0.7 cm. Diameter: 0.1 to 0.2 cm. Color: RHS Yellow-Green 144B. Texture: Glabrous.

FLOWER

Natural flowering season: All seasons, all year in Beit Dagan, Israel.
Days to flowering from rooted cutting: 30 days.
Inflorescence and flower type and habit: Axillary, single flower, salverform shape, upward and outwardly facing.
Rate of flower opening: 2 to 3 days from bud to fully opened flower.
Flower longevity on plant: 4 to 7 days.
Approximate quantity of flowers per plant: About 100.
Persistent or self-cleaning: Self-cleaning.
Bud:
*Shape*.—Ovoid.
*Length*.—12 cm.
*Diameter*.—0.4 cm.
*Color*.—RHS Yellow-Green 147B.
Flower size:
*Diameter*.—4 cm.
*Length*.—4.5 cm.
*Flower tube diameter at distal end*.—1 cm.
*Flower tube diameter at proximal end*.—0.3 cm.
Petals:
*Length from throat*.—2.3 cm.
*Size of marking of transition to flower throat upper surface*.—Medium.
*Width*.—1.4 cm.
*Quantity*.—5.
*Texture*.—Glabrous.
*Apex*.—Truncate.
*Margin*.—Entire.
*Lobing*.—Strong.
*Vein conspicuousness*.—Weak.
Color:
*When opening*.—Upper surface: RHS Red-Purple N74B. Lower surface: RHS Red-Purple N74D.
*Fully opened*.—Upper surface: RHS Red-Purple N74C. Lower surface: RHS Red-Purple N74D. Flower throat (inside): RHS Yellow 12B. Flower throat, vein: RHS Greyed-Orange 165D. Flower tube (outside): RHS Yellow 12D. Flower tube, vein: RHS Greyed-Orange 165A. Petal color, fading to: RHS Red-Purple N74D.
Calyx/sepals:
*Quantity per flower*.—5.
*Shape*.—Lanceolate.
*Length*.—1.1 cm.
*Width*.—0.3 cm.
*Apex*.—Rounded.
*Base*.—Cuneate.
*Margin*.—Entire.
*Texture*.—Upper surface: Glabrous. Lower surface: Glabrous.
*Color*.—Upper Surface: RHS Yellow-Green 147A. Lower Surface: RHS Yellow-Green 147B.
Peduncle: None present.
Pedicel:
*Length*.—2 cm.
*Diameter*.—0.1 cm.
*Color*.—RHS Yellow-Green 146D.
*Orientation*.—45 degrees.
Fragrance: None.

REPRODUCTIVE ORGANS

Stamens:
*Number*.—5.
*Filament length*.—0.4 to 0.6 cm.
Anthers:
*Length*.—0.1 cm.
*Shape*.—Globose.
*Color*.—RHS Yellow 12B.
*Pollen*.—Color: RHS Yellow 12C. Quantity: Medium.
Pistil:
*Number*.—1.
*Length*.—0.9 cm.
*Style*.—Length: 0.6 cm. Color: RHS Yellow-Green 146B.
*Stigma*.—Shape: Oblate. Color: RHS Yellow-Green 146B. Ovary Color: RHS Yellow-Green 146D.

OTHER CHARACTERISTICS

Seeds and fruits: About 30 dark brown, rounded seeds of about 0.5 mm diameter, per one brown, conical capsule.
Disease/pest resistance: Typical to known *Calibrachoa* varieties. Neither resistance nor susceptibility to the normal diseases and pests of *Calibrachoa* have been observed. Pests common to *Calibrachoa* include Aphids and thrips. Typical diseases are *Botrytis* and *Pythium*.
Temperature tolerance: 5° C. to 30° C.
Drought tolerance: No tolerance for drought.

What is claimed is:

1. A new and distinct cultivar of *Calibrachoa* plant named 'DCALBUBGM' as herein illustrated and described.

* * * * *